United States Patent
Iwamoto et al.

[11] Patent Number: 5,324,945
[45] Date of Patent: Jun. 28, 1994

[54] METHOD OF NONDESTRUCTIVELY MEASURING SUGAR CONTENT OF FRUIT BY USING NEAR INFRARED TRANSMITTANCE SPECTRUM

[75] Inventors: Mutsuo Iwamoto; Sumio Kono, both of Tsuchiura, Japan

[73] Assignee: Director of National Food Research Institute, Ministry of Agriculture, Forestry and Fisheries, Ibaraki, Japan

[21] Appl. No.: 936,590

[22] Filed: Aug. 27, 1992

[30] Foreign Application Priority Data

Oct. 4, 1991 [JP] Japan .................. 3-284174

[51] Int. Cl.$^5$ .................................. G01N 21/35
[52] U.S. Cl. ....................... 250/339.01; 250/341
[58] Field of Search .................... 250/334, 341

[56] References Cited

U.S. PATENT DOCUMENTS 4,883,953  11/1989  Koashi et al. ............... 250/341
5,089,701  2/1992  Dull et al. ................... 250/341

OTHER PUBLICATIONS

Dull et al, "Near Infrared Analysis of Soluble Solid in Intact Cantaloupe", J. Food Science, 54(2), Mar./Apr. 1989, pp. 393–395.
Article entitled "Determination of Sugars in Satsuma Orange Using NIR Transmittance", by Sumio Kawano, Tetsuo Sato and Mutsuo Iwamoto, published in Making Light Work: Advances in Near Infrared Spectroscopy, Ian Michael Pulblications, title pages, pp. 387–393, 1992.
Abstract of Lecture Given Aug. 19–23, 1991 in Aberdeen, Scotland entitled "Determination of Sugars in Satsuma Oranges using NIR Transmittance", by S. Kawano, T. Sato & M. Iwamoto, Aug. 1991.

Primary Examiner—Carolyn E. Fields
Attorney, Agent, or Firm—Frishauf, Holtz, Goodman & Woodward

[57] ABSTRACT

A method of nondestructively measuring the sugar content of fruit comprising irradiating the fruit with near infrared radiation such that the radiation penetrates the fruit; measuring the absorbance at a given wavelength with a wavelength selector that is placed in the optical path of the near infrared radiation; normalizing the obtained absorbance, taking account of the size of the fruit; and finding an index of the sweetness of the fruit from the normalized measured absorbance. Thus, the sugar content of fruits, especially of fruits having thick skins, can be measured nondestructively with practically acceptable accuracy.

1 Claim, 1 Drawing Sheet

METHOD OF NONDESTRUCTIVELY MEASURING SUGAR CONTENT OF FRUIT BY USING NEAR INFRARED TRANSMITTANCE SPECTRUM

FIELD OF THE INVENTION

The present invention relates to a method of nondestructively measuring the sugar content of fruit by the use of a near infrared (NIR) transmittance spectrum and, more particularly, to a method of nondestructively measuring the sugar content of fruit by passing NIR radiation through the fruit and measuring an index of the sweetness of the fruit.

BACKGROUND OF THE INVENTION

Research concerning nondestructive measurements of the sugar contents of fruits has been heretofore conducted by an indirect method. That is, the color of the skin of each fruit is measured, using visible radiation. Then, the degree of maturity is estimated from the color. However, this method assumes that a correlation exists between the color of the fruit skin and the sugar content of the fruit. Therefore, this method cannot be utilized for fruits where no correlation exists between them. In addition, even for fruits in which a correlation exists between the skin color and the sugar content, the correlation is affected greatly by cultivar, the conditions of the cultivation, and other factors. Consequently, the measuring accuracy is not very high.

In recent years, NIR spectroscopy which utilizes the phenomenon of absorption of NIR radiation, and has found wide application in determination of chemical components of grain and so forth, and has been applied to the measurements of sugar contents of fruits. It has been demonstrated that this method permits accurate measurements of sugar contents of fruits having thin skins such as peaches. In this case, diffuse reflected light at the surface of the skin and at the flesh layer close to the skin is used for the measurement. Therefore, it is impossible for this method to measure the sugar contents of fruits having thick skins.

SUMMARY OF THE INVENTION

Accordingly, the present invention is intended to provide a method of nondestructively and quickly measuring the sugar content (Brix value) of fruit having a thick skin such as a mandarin orange, etc. Fruits which have thick skins and whose sugar contents have been impossible or difficult to measure by the diffuse reflectance method include citrus fruits and kiwi fruits. The present invention can be applied also a watermelons and melons.

The present invention relates to a method of nondestructively measuring the sugar content of fruit, said method comprising the steps of: irradiating the fruit with NIR radiation such that the NIR radiation penetrates the fruit; measuring the absorbance at a given wavelength with a wavelength selector that is placed in an optical path of the NIR radiation; normalizing the measured absorbance, taking account of the size of the fruit; and finding an index of the sweetness of the fruit from the normalized absorbance.

DETAILED DESCRIPTION OF THE INVENTION

As a means of nondestructively measuring the sugar content of fruit having a thick skin, the present invention adopts a method comprising the steps of: irradiating the fruit with NIR radiation in the shorter wavelength region having a comparatively strong penetrating capability such that the NIR radiation penetrates the fruit; measuring the absorbance at a given wavelength with a wavelength selector that is placed in the optical path of the NIR radiation; normalizing the measured absorbance, taking account of the size of the fruit; and finding an index of the sweetness of the fruit from the normalized absorbance.

The novel method of nondestructively measuring the sugar content of each fruit having a thick skin comprises the successive steps described below.

Monochromatic radiation in the near infrared (NIR) region emerging from a monochromator or the like is directed to the skin of the fruit directly or by using fiber optics. The radiation penetrates through the fruit. The amount of light transmitted at an arbitrary wavelength is measured directly or by using fiber optics. In this way, the absorbance is measured. This measurement is repeated for a plurality of fruits. The absorbance increases as the concentration of the component under measurement increases. However, the absorbance measured by the transmittance method is affected by the size of the fruit as well as by the concentration of the component under measurement. Specifically, as the size of the fruit increases, the absorbance increases. Therefore, in order to find the sugar content of the fruit from the absorbance, it is necessary to remove the effect of the size of the fruit in advance.

It is known that a nearly linear relationship exists between the size of a fruit and the absorbance thereof. Therefore, we consider that the effect of the size of fruit can be eliminated by converting the absorbance into the absorbance of a fruit of the same size. One conceivable method of removing the effect of the size of a fruit on the absorbance is to divide the absorbance by the diameter of the fruit. In this method, it is necessary to measure the diameter of the fruit by a separate method. Hence, the measured items increase in number. Consequently, this method is not appropriate from a practical point of view. Accordingly, in the present invention, the wavelength at which the absorbance has a proportional relation to the diameter of the fruit is is searched for. The absorbance at a different wavelength is divided by the absorbance at the searched wavelength. The wavelength at which the absorbance has a proportional relation to the diameter of the fruit is next discussed. In the case of a mandarin orange, the absorbance has a strong correlation with the fruit diameter at a wavelength of 844 nm. At this wavelength the correlation with the sugar content is lowest. In consequence, this wavelength is preferable as a reference wavelength.

Figure 1:
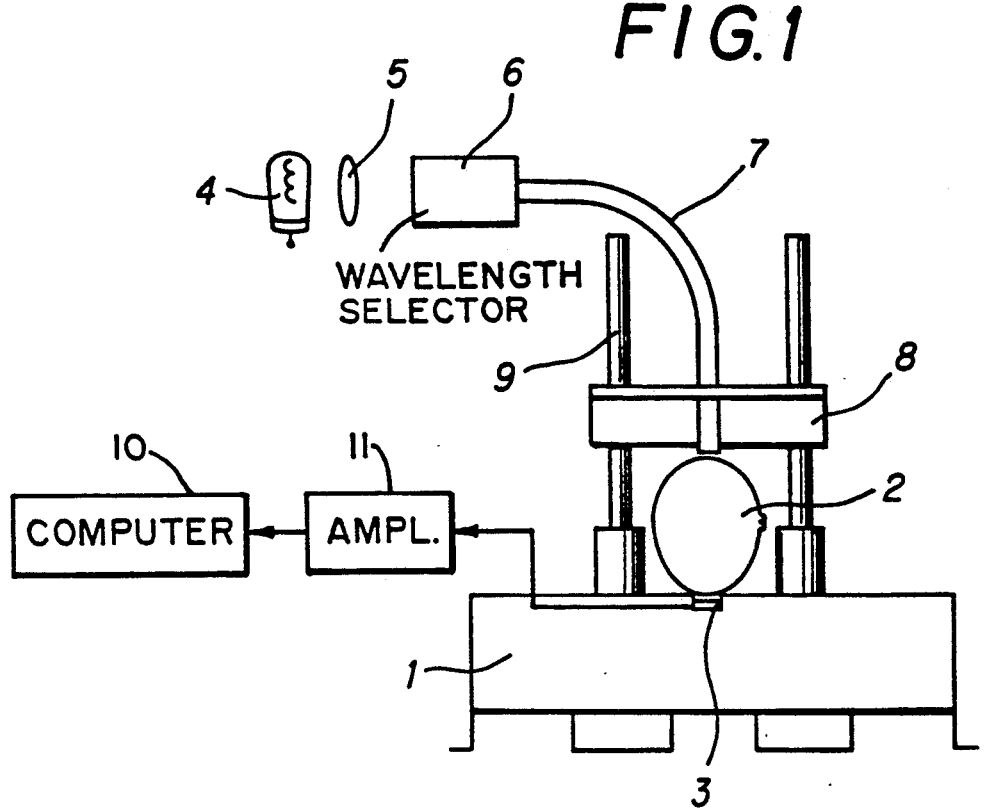
FIG. 1 is a front elevation of an instrument for measuring the absorbance of a fruit by the transmittance method, and in which the measurement is made from the equatorial portion of the fruit.
Figure 2:
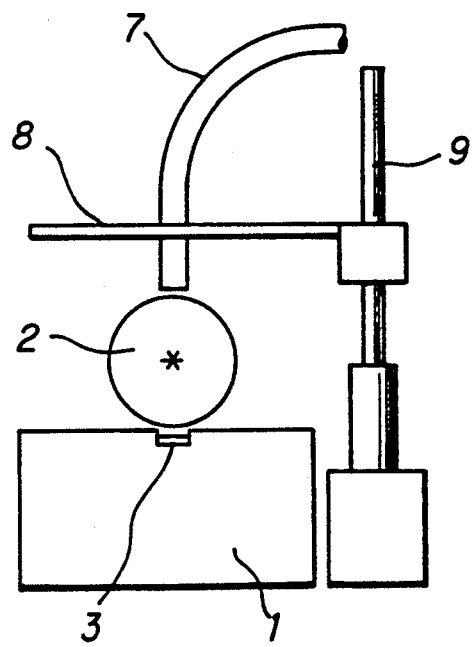
FIG. 2 is a side elevation of the instrument.

The novel method described above can be practiced using the instrument shown in FIGS. 1 and 2. First, a fruit 2 to be investigated is placed on a detection table 1. This table holds an optical sensor 3 such as a silicon detector and maintains the temperature of this sensor constant. Also, the table serves to hold a sample. The optical sensor 3 converts the intensity of light into a voltage. The output of the sensor 3 is connected to a computer 10 via an amplifier 11. The absorbance of the fruit may be detected at its equatorial portion or at its stem. In the case of a mandarin orange or the like, a more accurate measurement can be made at its equatorial portion. Near infrared light emitted from a light source 4 is dispersed by a wavelength selector 6 such as a monochrometer and guided to the skin of the fruit directly or by using a fiber optic light guide member 7. The light then penetrates through the fruit.

The fiber optic member 7 acts to guide the light emerging from the wavelength selector 6 to the fruit and usually comprises a bundle of glass fibers. The fiber optic member 7 is affixed to a mounting plate 8 which is mounted to support rods 9 which hold mounting plate 8 horizontally. The mounting plate 8 can slide on the support rods 9 in the up and down direction. The amount of light transmitted through the fruit 2 is measured at a given wavelength directly or by using fiber optics. Then, the absorbance is measured. Subsequently, a similar measurements are made for other fruits, and their absorbance are measured.

In the present invention, each obtained absorbance is normalized, taking the size of the fruit into consideration. The normalized absorbance used herein means the absorbance free of the effect of the size of the fruit. A multiple regression analysis is made using the data at the normalized absorbance and an index (e.g., of the Brix value measured by a refractometer). The multiple regression analysis can be automatically performed by a computer connected with a commercially available NIR instrument. By this calculation, equations given by the following model for determining an index of the sweetness are created.

Equation (1)

$$C = K_0 + K_1 L(\lambda_1) + K_2 L(\lambda_2) + K_3 L(\lambda_3) + \quad (1)$$

where C is an index of the sweetness, $K_0$, $K_1$, $K_2$, etc. are regression coefficients, and L ($\lambda_i$) is a normalized absorbance at a wavelength $\lambda_i$ (nm).

The absorbances of plural samples (for validation of a calibration equation) other than the sample used for calibration are measured by the same method as used for the measurement of the calibration sample. Normalized absorbances free of the effects of their sizes are calculated. An index of the sweetness is estimated from these normalized absorbances by the use of the above-described equation (1) obtained by the multiple regression analysis. The standard error of prediction (SEP) is computed. An equation which gives the least SEP is adopted as a calibration equation for estimating the sweetness of an unknown fruit.

Then, the obtained calibration equation is stored in the arithmetic portion of the instrument which measures the sweetness of fruit. In this way, the sugar content of the fruit can be estimated nondestructively with high reliability simply by measuring the absorbance of the fruit by the transmittance method.

The novel method described above can be applied to the case in which differentiated values calculated from normalized absorbances are used, as well as to the case in which normalized absorbances are used as optical data. This is, the first derivative value or the second derivative value, and so on of each normalized absorbance is used instead of the normalized absorbance. In particular, the term L($\lambda_i$) of equation (1) above changes to be the first derivative value or the second derivative value at a wavelength $\lambda_i$ (nm).

In accordance with the present invention, the sugar contents of fruits, especially of fruits having thick skins, can be measured nondestructively with practically acceptable accuracy, using NIR radiation.

The novel method of this invention permits the sugar contents of fruits to be nondestructively measured without being affected by the cultivar, the sizes, the conditions of cultivation, or other factors. Hence, the method of this invention is excellent in practicality.

The present invention will be explained in more detail by way of the following examples, which, however, are not intended to restrict the scope of the present invention. Example NIR transmittance spectra of 50 intact mandarin oranges were measured by the method illustrated in FIG. 1. The measurements were made at the equatorial portions and at the stems. Simultaneously, the sugar contents (Brix values) of their juice were measured with a refractometer PR-1 manufactured by Atago Co., Ltd. To remove the effects of their sizes on the measured spectra, each second derivative spectra was divided by the second derivative of the absorbance at a wavelength having a strong correlation with the size. In this way, the second derivative spectra were normalized, i.e., the effects of their sizes were removed.

A multiple regression analysis was performed for creating equations used to estimate the sweetness of the juice from the spectral data, based on the normalized second derivative spectra and the sugar contents of the juice. The results are shown in Table 1.

TABLE 1

| measuring portion | Results of calibration and validation | | | | | | | |
|---|---|---|---|---|---|---|---|---|
| | wavelength selected (nm) | | | | | | | |
| | $\lambda_1$ | $\lambda_2$ | $\lambda_3$ | $\lambda_4$ | R | SEC | SEP | Bias |
| equatorial portion | 914 | 769 | 745 | | 0.971 | 0.44 | 0.45 | −0.01 |
| | 914 | 769 | 745 | 786 | 0.989 | 0.28 | 0.32 | −0.02 |
| stem | 919 | 770 | 745 | | 0.941 | 0.61 | 0.71 | 0.10 |
| | 919 | 770 | 745 | 785 | 0.979 | 0.37 | 0.48 | 0.04 |

(Intact fruits were used. Corrected second derivative spectra were used.)

In Table 1, the wavelength selected is the wavelength $\lambda_i$ selected in each term of the right side of equation (1). R is the multiple correlation coefficient between a Brix value calculated from NIR spectra, using the equation obtained and the actual value measured with a refractometer. R ranges from −1 to 1. It follows that as the absolute value of multiple correlation coefficient (R) approaches unity, the measuring accuracy is enhanced. SEC is the standard deviation of each fitted value from the actual value. As this deviation decreases, the produced error decreases.

In a multiple regression analysis, as the wavelength selected for the calibration equation is increased, the standard error of calibration (SEC) decreases. As a result, the apparent measuring accuracy is improved. This is because the equation is mathematically fitted to the sample used for calibration. The equation obtained in this way loses generality and fails to fit to other samples. This phenomenon is known as "over fitting".

It can be known whether the obtained equation provides the over fitting or not by calculating the standard error of prediction (SEP) using samples other than the sample used for calibration.

NIR transmittance spectra of 50 intact mandarin oranges other than those used for calibration were measured by the above-described method, using the instrument shown in FIGS. 1 and 2, in the same way as when the deliberation equation is created. At the same time, the sugar content (Brix value) of the juice was measured with the refractometer. Then, normalized second derivative spectra were calculated. The SEP between the NIR predicted value and the actual value was calculated. Also, Bias, which is the difference between them, was calculated. These values are listed in Table 1 above. If the value of SEP increases with increasing the number of the wavelength selected, then over fitting is judged to occur. However, such a tendency was not observed in Table 1. Also, the values of Bias were small. That is, all the equations listed in the Table 1 hold generality. In addition, the equations are stable and keep Bias small. Among the equations, the equations containing optical data at four wavelengths of 914, 769, 745, and 786 nm showed the highest measuring accuracy.

With respect to the direction of measurements of fruits, higher measuring accuracy was obtained when measurements were made at the equatorial portions of the fruits than when measurements were made at the stems. This is explained away as follows. The sugar content of a mandarin orange differs slightly among segments. In the former type of measurement, the radiation passes through numerous segments. In the latter type of measurement, the radiation passes through only one segment.

The equations containing optical data at four wavelengths of 914, 769, 745, and 786 nm are given below.

Equation 2

$$C = -6.21 - 0.448L(914) + 84.853L(769) - 10.790L(745) - 71.887L(786)$$

where

Equation 3

$$L(\lambda) = d^2 \log(1/T\lambda)/d^2\log(1/T_{844})$$

Examples of a prediction of sugar content made when this equation as used as a calibration equation for unknown samples are shown in Table 2.

TABLE 2

Examples of prediction of Brix value of intact mandarin oranges

| sample number | predicted value | actual value | error |
|---|---|---|---|
| 1 | 7.30 | 7.70 | −0.40 |
| 2 | 8.22 | 8.20 | 0.02 |
| 3 | 8.71 | 8.50 | 0.21 |
| 4 | 9.41 | 9.40 | 0.01 |
| 5 | 9.67 | 9.70 | −0.03 |
| 6 | 10.16 | 10.00 | 0.16 |
| 7 | 10.62 | 10.30 | 0.32 |
| 8 | 11.03 | 11.10 | −0.07 |
| 9 | 11.34 | 11.30 | 0.04 |
| 10 | 12.31 | 12.00 | 0.31 |
| 11 | 12.47 | 12.50 | −0.03 |
| 12 | 13.53 | 13.70 | −0.17 |
| 13 | 13.59 | 13.70 | −0.11 |
| 14 | 14.39 | 14.80 | −0.41 |
| 15 | 14.95 | 14.50 | 0.45 |

As can be seen from Table 2, the difference between the NIR predicted value and the actual value is small. Consequently, the predicted value can be used with practically high accuracy.

What is claimed is:

1. A method of nondestructively measuring the sugar content of fruit, comprising the steps of:

irradiating the fruit with near infrared radiation such that the near infrared radiation penetrates the fruit;

measuring a radiation transmitted through the fruit to obtain a spectrum of the absorbance at a given wavelength region with a wavelength selector that is placed in a direct optical path of the near infrared radiation;

differentiating said measured absorbance spectrum to obtain a second derivative absorbance spectrum;

dividing said second derivative absorbance spectrum by a second derivative value of absorbance measured at a wavelength having a strong correlation with the size of the fruit, to obtain a normalized second derivative spectrum of absorbance where the effects of size of the fruit are removed; and finding an index of the sweetness of the fruit from said normalized second derivative spectrum of absorbance.

* * * * *

UNITED STATES PATENT AND TRADEMARK OFFICE
CERTIFICATE OF CORRECTION

PATENT NO. : 5,324,945

DATED : June 28, 1994

INVENTOR(S) : IWAMOTO et al

It is certified that error appears in the above-identified patent and that said Letters Patent is hereby corrected as shown below:

Title page, Item [75] Inventors, "Kono" should be --Kawano--

Column 6, line 42, "where" should be --wherein--

Signed and Sealed this

Nineteenth Day of September, 1995

Attest:

BRUCE LEHMAN

*Attesting Officer*      *Commissioner of Patents and Trademarks*